(12) United States Patent
Province et al.

(10) Patent No.: US 6,256,535 B1
(45) Date of Patent: Jul. 3, 2001

(54) METHOD FOR DELIVERING CARDIAC THERAPY AND A CARDIAC THERAPY DEVICE FOR IMPLEMENTING THE SAME

(75) Inventors: Rose Province, San Jose; Benjamin D. Pless, Atherton, both of CA (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

(21) Appl. No.: 09/342,796

(22) Filed: Jun. 29, 1999

(51) Int. Cl.$^7$ ...................................................... A61N 1/39
(52) U.S. Cl. .................................................................. 607/5
(58) Field of Search ................................. 607/5, 9, 13, 14

(56) References Cited

U.S. PATENT DOCUMENTS 5,161,528 * 11/1992 Sweeney .
6,085,116 * 7/2000 Pendekanti et al. .

* cited by examiner

*Primary Examiner*—Scott M. Getzow
(74) *Attorney, Agent, or Firm*—Steven M. Mitchell (57) ABSTRACT

A method for delivering cardiac therapy, particularly defibrillation therapy, using an implantable cardioverter-defibrillator (ICD) or other cardiac therapy device. The method can be used either alone or in conjunction with any other suitable defibrillation (or other cardiac) therapy regimen. If used in conjunction with a conventional or other suitable defibrillation therapy regimen, the method can be considered to precondition the heart in advance of delivery of the defibrillation shock(s), in order to reduce the defibrillation threshold (DFT), and thus reduce the overall energy required for delivery of effective defibrillation therapy. In either case, in accordance with the method, the voltage gradients (VGs) across a plurality of different regions of the heart are sensed, e.g., using an endocardial sensor array (ESA), and a respective plurality of electrograms (EGMs) are produced in respective EGM channels. The excitable gaps (i.e., the intervals between successive activations) in the different VG regions of the heart are then brought into phase alignment with one another by appropriately timing the delivery of electrical stimulation (e.g., one or more pulses). In this connection, either the timing of the next activation interval can be advanced by delivering an electrical stimulus (pulse) during the excitable gap or in the late repolarization phase of the previous activation, or the activation interval can be extended by delivering an electrical stimulus earlier in the repolarization phase of the previous activation, leading to an extension of the refractory period (i.e., RPE). If three or more EGM channels are used, the excitable gaps in the different VG regions are preferably brought into phase with one another by first bringing the region associated with the near-field EGM channel into phase alignment with the region associated with the EGM channel of the adjacent (next highest) VG region and then successively entraining the thusly entrained regions with the regions associated with the EGM channels corresponding to the successively more distant VG regions, until the regions associated with all EGM channels are brought into phase alignment with one another. Also disclosed is a cardiac therapy device (e.g., an ICD) for implementing this method.

27 Claims, 4 Drawing Sheets

METHOD FOR DELIVERING CARDIAC THERAPY AND A CARDIAC THERAPY DEVICE FOR IMPLEMENTING THE SAME

BACKGROUND OF THE INVENTION

The present invention relates generally to implantable cardioverter defibrillators, and, more particularly, to a method for delivering cardiac therapy (e.g., defibrillation/shock therapy), and a cardiac therapy device (e.g., an ICD) for implementing the same.

Implantable cardioverter defibrillators (ICDs) are sophisticated medical devices which are surgically implanted (abdominally or pectorally) in a patient to monitor the cardiac activity of the patient's heart, and to deliver electrical stimulation as required to correct cardiac arrhythmias which occur due to disturbances in the normal pattern of electrical conduction within the heart muscle. Cardiac arrhythmias can generally be thought of as disturbances of the normal rhythm of the heart beat. Cardiac arrhythmias are broadly divided into two major categories, namely, bradyarrhythmia and tachyarrhythmia. Tachyarrhythmia can be broadly defined as an abnormally rapid heart rate (e.g., over 100 beats/minute, at rest), and bradyarrhythmia can be broadly defined as an abnormally slow heart rate (e.g., less than 50 beats/minute). Tachyarrhythmias are further subdivided into two major sub-categories, namely, tachycardia and fibrillation. Tachycardia is a condition in which the electrical activity and rhythms of the heart are rapid, but organized. Fibrillation is a condition in which the electrical activity and rhythm of the heart are rapid, chaotic, and disorganized. Tachycardia and fibrillation are further classified according to their location within the heart, namely, either atrial or ventricular. In general, atrial arrhythmias are not life-threatening, because the atria (upper chambers of the heart) are only responsible for aiding the movement of blood into the ventricles (lower chambers of the heart), whereas ventricular arrhythmias are life-threatening, because if the ventricles become arrhythmic, the heart's ability to pump blood to the rest of the body is impaired. The most serious and immediately life-threatening type of cardiac arrhythmia is ventricular fibrillation, in which the electrical activity of the ventricles becomes so random and chaotic that the heart rapidly becomes unable to pump sufficient blood to sustain life.

In general, an ICD continuously monitors the heart activity of the patient in whom the device is implanted by analyzing electrical signals, known as electrograms (EGMs), detected by endocardial (intracardiac) sensing electrodes positioned in the right ventricular apex and/or right atrium of the patient's heart. More particularly, contemporary ICDs include waveform digitization circuitry which digitizes the analog EGM produced by the sensing electrodes, and a microprocessor and associated peripheral ICs which analyze the digitized EGM in accordance with a diagnostic algorithm implemented by software stored in the microprocessor. Contemporary ICDs are generally capable of diagnosing the various types of cardiac arrhythmias discussed above, and then delivering the appropriate electrical stimulation/therapy to the patient's heart, in accordance with a therapy delivery algorithm also implemented in software stored in the microprocessor, to thereby correct or terminate the diagnosed arrhythmia.

In this connection, contemporary ICDs are capable of delivering various types or levels of electrical therapy. The first type of therapy is bradycardia and antitachycardia pacing, in which a low level of electrical energy (generally between millionths to thousandths of a joule) is delivered to the patient's heart in order to correct detected episodes of bradycardia or tachycardia, respectively. The second type of therapy is cardioversion, in which an intermediate level of electrical energy (generally between 1–5 joules) is delivered to the patient's heart in order to terminate a detected episode of ventricular tachycardia (e.g., a detected heart beat in the range of 130–190 beats/minute) or an ongoing episode of tachycardia that antitachycardia pacing has failed to correct or terminate. The third type of therapy is defibrillation, in which a high level of electrical energy (generally above 15 joules) is delivered to the patient's heart in order to abort a detected episode of ventricular fibrillation or an episode of ventricular tachycardia which has degraded into ventricular fibrillation due to failure of cardioversion therapy.

The provision of the above-described different types or levels of therapy is generally referred to in the art as "tiered therapy". In this regard, contemporary ICDs which are capable of delivering tiered therapy are sometimes referred to as combination pacemakers/defibrillators or as implantable cardioverter-defibrillators. As used herein, the terminology "implantable cardiac defibrillator" (ICD) is intended to encompass these and other forms and types of implantable cardiac therapy devices.

Current-generation ICDs which are capable of delivering tiered therapy provide several advantages over previous-generation ICDs which were only capable of delivering high energy defibrillation therapy. Namely, ICDs which are capable of delivering tiered therapy are generally more energy-efficient, since they can deliver much lower energy therapy, such as antitachycardia pacing and cardioversion, to terminate many arrhythmia events before they degrade into a ventricular fibrillation event. The much higher energy defibrillation therapy is only necessary when these lower energy therapies fail to abort the arrhythmia. Thus, tiered therapy conserves the energy stored in the battery(ies) of the device, thereby extending the longevity of the device, and also enables a significant portion of potential ventricular fibrillation events to be aborted with lower energy therapy which is much less painful and uncomfortable to the patient.

A primary goal in the design and further development of ICDs is to ensure delivery of effective therapy with a minimum expenditure of energy. Reduction of the total energy required to deliver effective therapy enables the size of the batteries and capacitors used in the ICDs to be reduced, thereby enabling a commensurate reduction in the size of the ICD. The benefits to the patient are two-fold. First, the use of lower voltage cardioversion and defibrillation therapy reduces patient pain and discomfort during delivery of such therapy, and second, the reduction in the size of the ICD decreases patient discomfort due to the physical pressure exerted by the ICD within the patient's body. A further benefit is that the longevity of the device can be extended for a given power supply. Additionally, the smaller the ICD, the easier it is to implant the device using minimally invasive surgery, thereby decreasing the cost of implantation. In this regard, it is highly preferable that the ICD be at least small enough to be implanted pectorally, rather than abdominally, without sacrificing functionality, because pectoral implantation requires much less invasive surgery than abdominal implantation. Consequently, pectoral implantation is both much less costly and much more comfortable to the patient (both at the time of implantation and thereafter), than abdominal implantation.

One of the major areas of ongoing R&D within the field of ICDs is the development of increasingly sophisticated diagnostic and therapy delivery algorithms, which enable the above-stated primary ICD design goal to be realized by optimizing the therapeutic efficacy of the device. More particularly, in accordance with the diagnostic algorithm, the microprocessor and associated peripheral ICs continuously monitor the digitized EGMs in order to sense or detect various features thereof, e.g., waveform slope (dv/dt), waveform minima and maxima, intervals between specified cardiac events, etc., which are indicative of various prescribed cardiac events, e.g., (P)QRS complexes, depolarization, repolarization, tachycardia, bradycardia, fibrillation, etc.

When a specified cardiac event is detected, the microprocessor, under the control of the therapy delivery algorithm, then triggers and controls the delivery of therapy, e.g., synchronous with (i.e., generally time-related to) such sensed features of the EGMs and/or cardiac events, in order to avoid inducing a degeneration to fibrillation in a tachycardia episode (i.e., arrhythmogenesis). In this regard, therapy is generally delivered (by the output or current delivery stage of the ICD, under microprocessor control) as a sequence of one or more electrical pulses, the timing, number, shape, tilt, magnitude, duration, and/or polarity (and/or other characteristics) of which are controlled in accordance with the therapy delivery algorithm in such a manner as to optimize therapeutic efficacy. The optimum values of the parameters or variables used in these algorithms may vary from one patient to the next, depending on the individual patient's particular cardiac condition and/or history.

Although the presently known therapy delivery algorithms have proven effective, it is believed that there is still room for improvement, and, more particularly, for a therapy delivery algorithm that ensures delivery of effective therapy with even lower energy requirements. In this connection, the present invention, in one of its aspects, is directed to a different approach to delivery of cardiac therapy in which the electrical activity in different regions of the heart is sensed and compared, and in which the timing of the electrical stimuli delivered to the heart is related to the results of the comparison. The present invention, in another of its aspects, is directed to a different approach to delivery of cardiac therapy in which activation intervals in different regions of the heart are selectively shortened or lengthened, based upon the sensed electrical activity in the different regions, to thereby reduce the energy required to terminate detected arrhythmias, e.g., to lower the defibrillation threshold (DFT) and thus, the overall energy required to deliver effective defibrillation therapy.

The following definitions and brief review of pertinent aspects of cardiology is designed to facilitate a better understanding of the ensuing description of the present invention. Starting first with the definitions, the term "electrogram" as used herein means "an extracellular unipolar or bipolar recording or a monophasic action potential (MAP)". The term "voltage gradient" as used herein means "the voltage across tissue that is created when a field stimulus is applied (measured in volts per centimeter)".

The term "action potential" as used herein means "a transient change in electric potential across the membrane of a myocardial cell in response to either an intrinsic or extrinsic electrical stimulus". The term "activation" as used herein means "the depolarization of tissue (phase 0 of action potential) locally to an electrogram". The term "refractory period" as used herein means "a period of time following an activation during which cardiac tissue repolarizes and will not produce a new activation in response to a further electrical stimulus (absolute refractory period), or will only produce a new activation in response to a further stimulus having a higher amplitude (relative refractory period). Further, the "refractory period" is a period during which an extension of the repolarization time of the tissue can occur, in response to an electrical stimulus which is not strong enough to produce a new activation, a phenomenon known as "refractory period extension".

Figure 1:
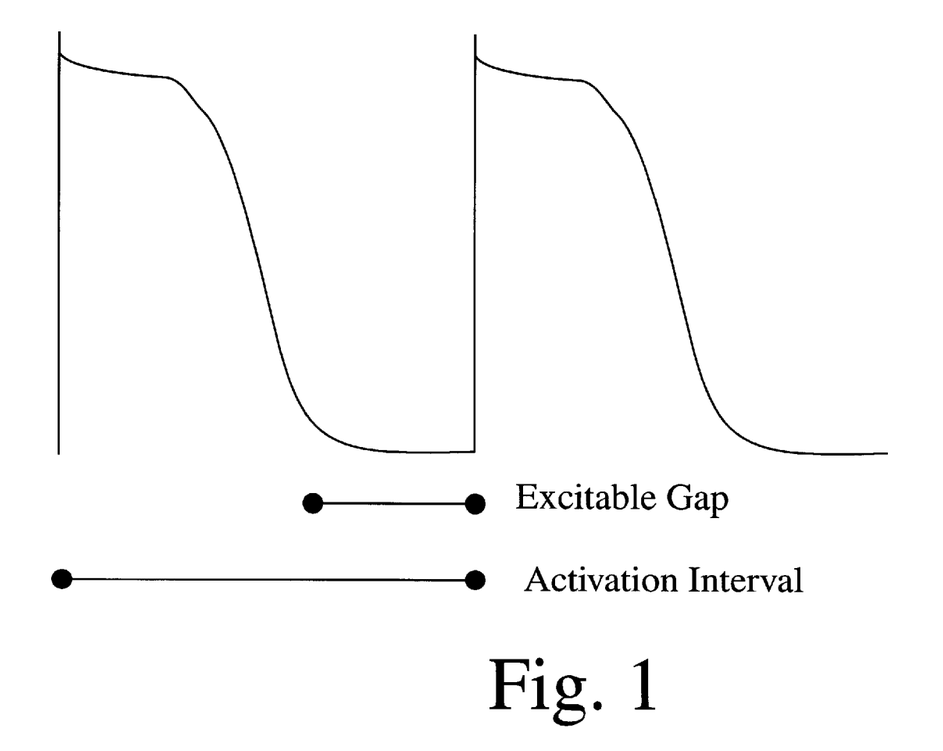
FIG. 1 is a waveform diagram depicting an "excitable gap" and an "activation interval"

The time period when a refractory period extension is induced is part of what has been previously clinically defined as an "absolute refractory period". As used herein, however, the term "refractory period" shall mean the entire period from the time that any refractory period extension can be induced by external stimuli until the time that the tissue has recovered complete excitability. The term "excitable gap" as used herein means "the period following an activation when tissue local to an electrogram recovers complete excitability". Thus, as used herein, "excitable gaps" correspond to the time periods (intervals) between successive activations, as can be seen in FIG. 1.

With ventricular tachycardia, a shortening of the normal cardiac cycle is experienced (i.e., the interval between successive heartbeats or "QRS complexes" decreases), thereby resulting in an elevated heart rate. Although the heart rate is elevated, the electrical activity of the myocardial cells distributed throughout the heart tissue is generally synchronous, i.e., the excitable gaps are generally synchronized, thereby stimulating the heart muscle to rhythmically contract and relax, to thereby produce successive heart beats, albeit at an elevated heart rate.

Atrial and ventricular fibrillation consist of multiple wavefronts traversing the heart at once. It has been shown that these wavefronts both converge and break up, creating periods of higher and lower organization. As will become apparent hereinafter, a goal of the therapy method of the present invention is to organize these wavefronts with a minimum amount of energy.

When a defibrillation shock is delivered by a shock delivery electrode, different voltage gradients are produced across different local regions of the heart, with the magnitude of the voltage gradients decreasing as a function of distance and position relative to the delivery electrodes, with the highest voltage gradient occurring right at the tissue/electrode interface. Thus, the voltage gradient (VG) across a region of the heart near the electrodes (hereinafter referred to as the "near-field region") will be significantly higher than the VG across a region of the heart which is more distant from the electrodes (hereinafter referred to as the "far-field region"). It is known that delivery of a pulse during the latter part of the refractory period of an action potential can prolong the duration of the action potential, and that the extent of the action potential prolongation is dependent upon the specific timing of the pulse (particularly with respect to the degree of membrane "repolarization") and the magnitude of the VG across the myocardial cells, so long as the magnitude of the pulse does not exceed a threshold level which, if exceeded, would create a new action potential.

It has been established that the above-described refractory period extension (RPE) or action potential prolongation is enhanced by delivering shocks having a biphasic waveform, as opposed to a monophasic waveform. See, e.g., the article entitled "Biphasic Defibrillation Waveforms Reduce Shock-Induced Response Duration Dispersion Between Low and High Shock Intensities", by Oscar H. Tovar, Janice L. Jones, Circ. Res. 1995; 77:430–438. In this regard, it is believed that the biphasic waveform reduces the disparity in shock-induced response durations between low and high voltage gradients as compared with the monophasic waveform. In other words, it is believed that the biphasic waveform produces a more uniform RPE of the action potentials in the different LVG regions of the heart. It has also been established that the RPE increases the later in the refractory period in which the shock is delivered. See, e.g., the article entitled "Ventricular Refractory Period Extension Caused by Defibrillation Shocks", by Robert J. Sweeney et al., *Circulation* 1990; 82:965–972.

It has also been shown that RPE is a very transient rescheduling of the cellular repolarization process, which is consistent with the hypothesis that RPE may result from a local graded response of the cells to the shock stimulus. It has further been shown that RPE is confined to the repolarization phase in which the shock is delivered, and that it is not caused by a transient change in cellular excitability.

The myocardial cells of different regions of the heart are in different phases of the action potential during fibrillation. In addition, a defibrillation shock creates differing VGs across different regions of the heart. Therefore, the shock can induce a wide variety of cellular responses simultaneously, either prolonging the refractory period so that the myocardial cells block re-entrant fibrillation wavefronts from propagating, or induce activations which can create new re-entry, or have no effect, such as when a shock is delivered in the early refractory period of cardiac tissue. Because of this, a shock can lead to refibrillation.

The "upper limit of vulnerability" hypothesis states that the shock must be strong enough to limit the "dispersion of refractoriness" below a critical threshold which leads to refibrillation. Of course, increasing the required strength of the shock (i.e., increasing the defibrillation threshold (DFT) and the defibrillation energy requirements) is just the opposite of the desired goal of defibrillation therapy. For successful defibrillation, it is believed that there must be a decrease in the dispersion of repolarization. As will become fully apparent hereinafter, the therapy delivery method of the present invention attempts to decrease the dispersion of repolarization by shortening and extending activation intervals in different regions of the heart, with the goal (in the presently preferred embodiment) of synchronizing the electrical activity throughout the entire heart.

SUMMARY OF THE INVENTION

In overview, the present invention relates to a method for delivering cardiac therapy, particularly defibrillation therapy, using an implantable cardioverter-defibrillator (ICD) or other cardiac therapy device. The method of the present invention can be used either alone or in conjunction with any other suitable defibrillation (or other cardiac) therapy regimen. If used in conjunction with a conventional or other suitable defibrillation therapy regimen, the method of the present invention can be considered to precondition the heart in advance of delivery of the defibrillation shock (s), in order to reduce the defibrillation threshold (DFT), and thus reduce the overall energy required for delivery of effective defibrillation therapy.

In either case, in accordance with the present invention, the voltage gradients (VGs) across a plurality of different regions of the heart are sensed, e.g., using an endocardial sensor array (ESA), and a respective plurality of local electrograms (EGMs) are produced in respective EGM channels.

In accordance with one aspect of the present invention, activation intervals in different regions of the heart are selectively shortened or lengthened, based upon the sensed electrical activity in the different regions.

In accordance with another aspect of the present invention, the electrical activity in different regions of the heart (i.e., local or "sub-global" cardiac activity) is sensed and compared, and electrical stimuli are delivered to the heart with a timing based upon the results of the comparison.

More particularly, in a presently preferred embodiment, the excitable gaps in the different regions of the heart are brought into phase with one another by appropriately timing the delivery of electrical stimulation (e.g., one or more pulses). In this connection, the excitable gap can either be decreased by delivering an electrical stimulus (pulse) during the excitable gap or in the late repolarization phase of the previous action potential, or delayed by delivering an electrical stimulus earlier in the repolarization phase of the previous action potential, leading to extension of its refractory period (i.e., RPE).

If three or more regions (and thus, three or more "EGM channels") are used, the excitable gaps in the different regions of the heart are preferably bringing the region nearest the delivery electrode and the adjacent region (i.e., the region next nearest the delivery electrode) into phase with another (i.e., into a phase coherent relationship), and then bringing the successively more distant regions into phase with another until all regions are in phase with another. This process can be viewed as successive entrainment or capture of successive different regions of the heart located at incrementally greater distances from the delivery electrode. Alternatively, this process can be viewed as "synchronizing" the successive "EGM channels" associated with these successive different regions of the heart.

When all regions are in phase, the excitable gaps in each of the plurality of regions of the heart will also be in phase, thereby rendering all of these different regions of the heart refractory to re-entrant fibrillation wavefronts at the same time, and responsive to electrical stimuli at the same time.

Thus, after all regions are brought into phase with one another, the ventricular fibrillation is either intrinsically converted into ventricular tachycardia, which can be terminated by the delivery of any suitable cardioversion therapy, or is terminated by the delivery of any suitable defibrillation therapy.

BRIEF DESCRIPTION OF THE DRAWINGS

These and other objects, features, and advantages of the present invention will be readily understood from the following detailed description taken in conjunction with the accompanying drawings, in which.

DETAILED DESCRIPTION OF THE INVENTION

While the present invention is described herein with reference to an illustrative embodiment for a particular application, it should be understood that the present invention is not limited thereto. Those having ordinary skill in the art and access to the teachings provided herein will recognize additional modifications, applications, and embodiments within the scope thereof and additional fields in which the present invention would be of significant utility.

At the outset, it should be recognized that the method for delivering cardiac therapy in accordance with the present invention can be used either alone or in conjunction with any other suitable cardiac therapy algorithm. Further, although the method of the present invention is described hereinafter with respect to delivery of defibrillation therapy, it should also be recognized that the method is not limited to this particular type or level of therapy.

Figure 2:
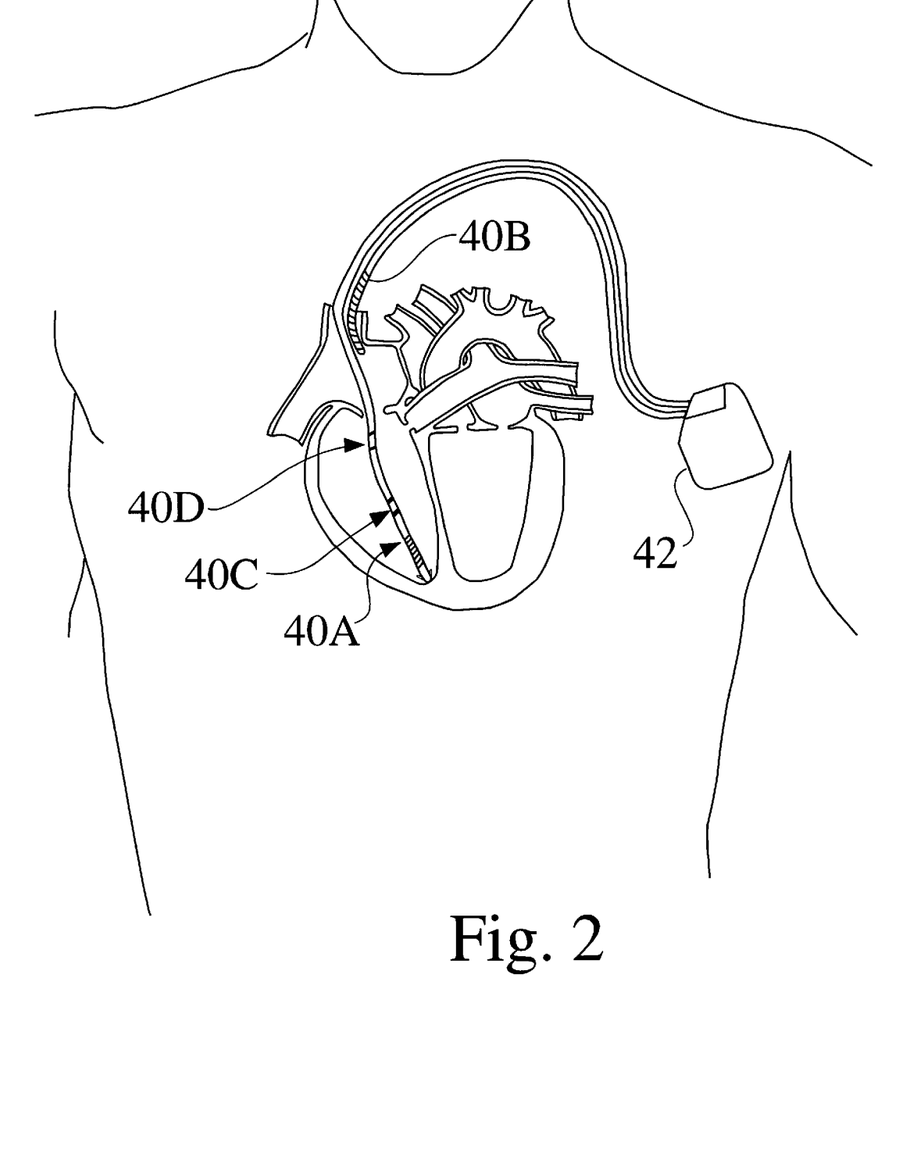
FIG. 2 illustrates the placement of an implantable cardioverter-defibrillator and electrode system in the pectoral region of a patient.

With reference now to FIG. 2, delivery electrodes 40A, 40B, are placed in the apex of the right ventricle and in the right atrium of a patient's heart, respectively. Of course, any other suitable electrode configuration can be employed in addition to or in lieu of the one depicted in FIG. 2. For example, an active can may be utilized in conjunction with one or more of the delivery electrodes 40A, 40B. Further, sensing electrodes 40C, 40D are placed proximate to different, respective local regions of the patient's heart in order to detect respective local electrograms (EGMs), in respective EGM channels. The sensing electrodes 40C, 40D are placed so that it is possible to sense from tissue both at high and low voltage gradients when the field stimulation is applied. The respective local EGMs are indicative of successive activations and the excitable gaps therebetween which occur in the respective local regions of the patient's heart. An activation is detected when the amplitude of the derivative of the unipolar EGM crosses a prescribed threshold. The detection of the activation using a unipolar EGM recording is preferably done by taking a derivative over a 5-point data window. The respective local EGMs are digitized by conventional waveform digitization circuitry (not shown) of an ICD 42 implanted in the chest or abdomen of the patient, in a conventional manner well-known in the art.

The digitized local EGMs are then processed by digital signal processing circuitry (e.g., a microprocessor and associated control logic circuitry) of the ICD 42. The digital signal processing circuitry generates control signals which are applied to a pulse delivery circuit (not shown) which delivers the therapeutic pulses or shocks to the patient's heart via one or more pulse delivery electrodes (e.g., sensing/pulse delivery electrode 40A) in response to these control signals. In this connection, the digital signal processing circuitry controls the delivery of the cardiac therapy (e.g., defibrillation therapy) by generating the control signals in accordance with a program stored therein.

In accordance with the present invention, the ICD 42 is preferably programmed to implement the method of delivering cardiac therapy of the present invention. In this regard, it is a routine matter to those of ordinary skill in the art to write the code constituting the software (computer program) for programming the ICD 42 (or other cardiac therapy device), using readily available programming tools.

Figure 3:
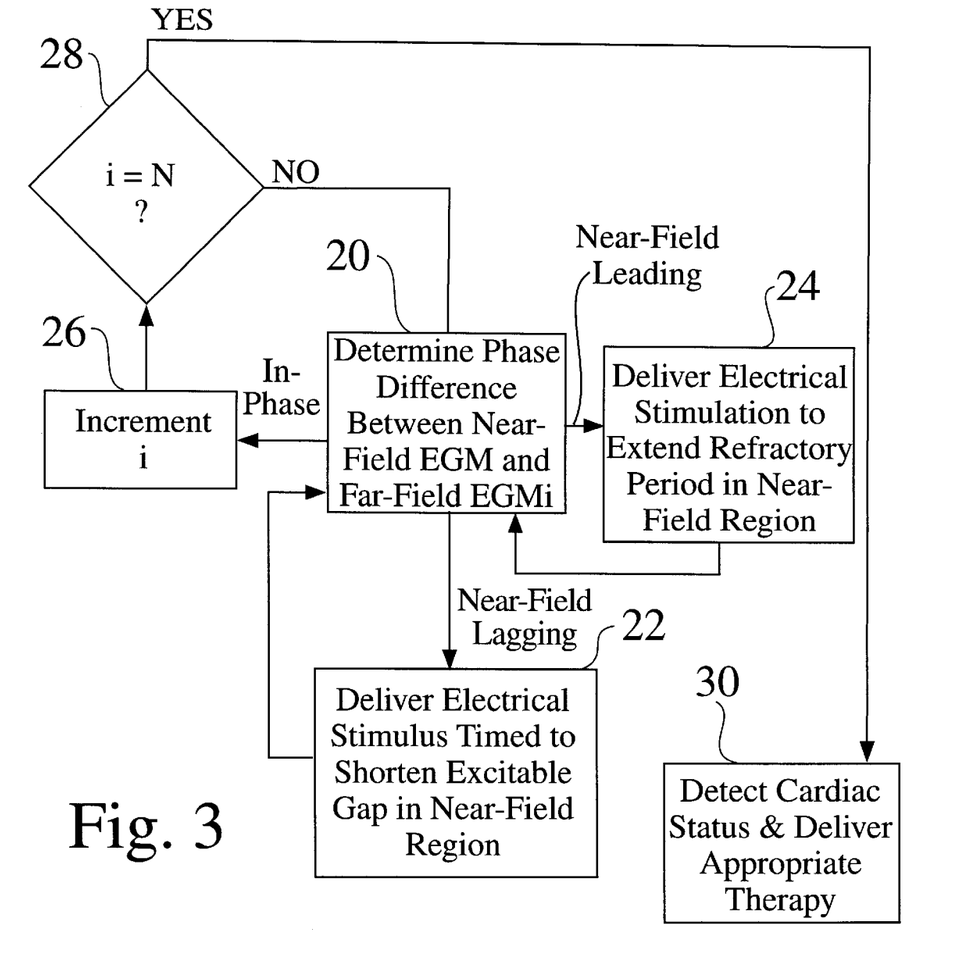
FIG. 3 is a flow chart illustrating a method of delivering cardiac therapy in accordance with a first preferred embodiment of the present invention.

With reference now to FIG. 3, there can be seen a flow chart illustrating a presently preferred embodiment of the method of the present invention. More particularly, at step 20, the phase difference between a first digitized local EGM and an additional digitized local EGMi is determined. Otherwise stated, the phase difference between the regions associated with the first and additional digitized local EGMi's is determined. In accordance with a presently preferred embodiment of the present invention, the first digitized local EGM is detected by the sensing electrode 40C nearest the pulse delivery electrode 40A, and is generally referred to as the "near-field" EGM. The additional digitized local EGMi is detected by the sensing electrode 40D further from the pulse delivery electrode 40A, and thus, is generally referred to as a "far-field" EGM.

Further, a plurality N of "additional" digitized sub-global EGMi's detected by respective sensing electrodes positioned at varying distances from the pulse delivery electrode can be utilized. In general, there will be a total of N+1 EGM channels, including the near-field EGM channel and N far-field EGM channels, and i=1 through N.

Figure 4:
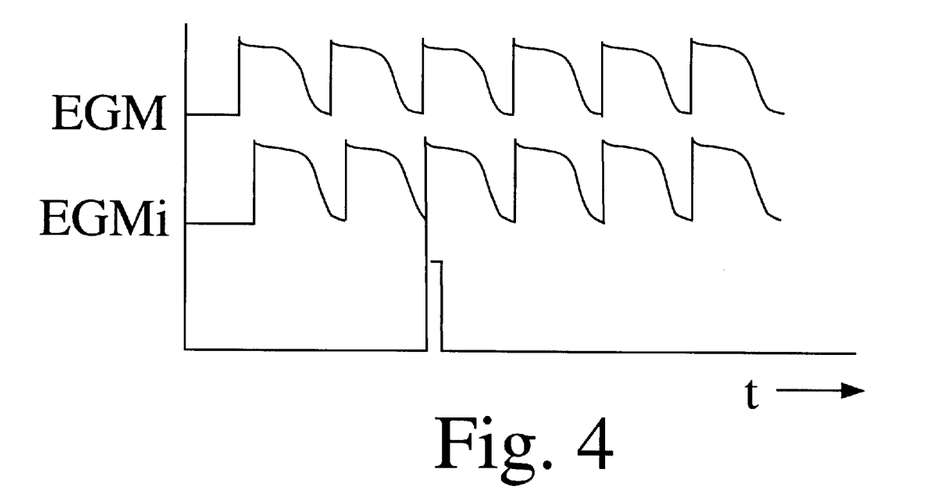
FIG. 4 is a timing diagram depicting the timing of the delivery of an electrical stimulus to bring the different regions associated with the near-field and far-field EGMs into phase with one another when it is detected that the region associated with the near-field EGM is phase-lagging the region associated with the far-field EGM; and, FIG. 5 is a timing diagram depicting the timing of the delivery of an electrical stimulus to bring the regions associated with the near-field and far-field EGMs into phase with another when it is detected that the region associated with the near-field EGM is phase-leading the region associated with the far-field EGM.

If it is determined in step 20 that the phase of the region associated with the near-field EGM is lagging the phase of the region associated with the far-field EGMi, then the method branches to step 22, in which an electrical stimulus (STIM) is applied via the delivery electrode to the patient's heart during the late repolarization phase of the next activation, or during the next excitable gap, as determined from the near-field EGM, in order to advance the timing of the next activation which occurs in the near-field local region of the patient's heart, and thus reduce the phase difference between the regions associated with the near-field EGM and the far-field EGMi, as is depicted in FIG. 4. In this connection, it is preferable that the near-field EGM be used as the reference for correcting the determined phase difference since the closer tissue can best be controlled by the electrical stimulus (STIM), as the closer tissue is exposed to a higher voltage gradient in response to the delivered electrical stimulus.

After delivery of the electrical stimulus (STIM), the method loops back to step 20 and the process is repeated until it determined that the regions associated with the near-field EGM and the far-field EGMi are in-phase. Optionally, an additional step (not shown) of adjusting (e.g., increasing) the voltage of the electrical stimulus can be employed if the regions associated with the near-field EGM and far-field EGMi are not brought into phase with each other after a prescribed number (e.g., 2–8) of unsuccessful attempts.

Figure 5:
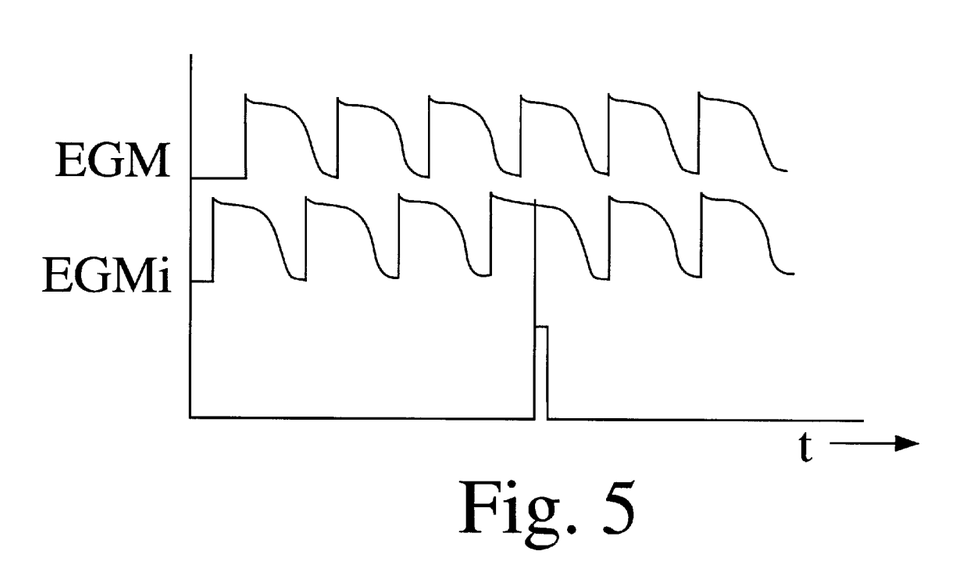

If it is determined in step 20 that the region associated with the near-field EGM is leading the far-field EGMi, then the method branches to step 24, in which an electrical stimulus ("STIM") is applied via the delivery electrode to the patient's heart during the refractory period of the next activation, as determined from the near-field EGM, in order to thereby extend the refractory period of the next activation which occurs in the near-field local region of the patient's heart, and thus reduce the phase difference between the regions associated with the near-field EGM and the far-field EGMi, as is depicted in FIG. 5. The electrical stimulus (STIM) is preferably a pulse having a voltage and a time delay relative to the last activation which is proportional to the determined phase difference between the regions associated with the near-field EGM and the far-field EGMi, since the refractory period of the near-field tissue is extended proportionally with the applied VG.

After delivery of the electrical stimulus (STIM), the method loops back to step 20 and the process is repeated until it determined that the regions associated with the near-field EGM and the far-field EGMi are in-phase (or nearly in-phase). Optionally, an additional step (not shown) of adjusting (e.g., increasing) the voltage of the electrical stimulus can be employed if the regions associated with the near-field EGM and far-field EGMi are not brought into phase (or nearly into phase) with each other after a prescribed number (e.g., 2–8) of unsuccessful attempts.

If it is determined in step 20 that the region associated with the near-field EGM is in-phase with the region associated with the far-field EGMi, then the method branches to step 26, in which i is incremented by 1. The method then proceeds to step 28, in which a determination is made as to whether i=N. If i≠N, then the method loops back to step 20, and the process is repeated for the next far-field EGMi. If i=N (i.e., the regions associated with all EGM channels have been determined to be in-phase), then the method branches to step 30, in which it is determined whether cardiac therapy is required, and, if so, what type of therapy. In this regard, if it is determined that the episode of fibrillation has been intrinsically converted to tachycardia by bringing the regions associated with the near-field and far-field EGM channels into phase alignment with each other, then cardioversion therapy can be delivered in any convenient manner well-known to those of ordinary skill in the art. If the fibrillation is detected as ongoing, then fibrillation therapy can be delivered in any convenient manner well-known to those of ordinary skill in the art. In this regard, as previously mentioned, the method of the present invention can be used to pre-condition the patient's heart in advance of delivery of the defibrillation shock(s), in order to thereby reduce the defibrillation threshold (DFT), and thus reduce the overall energy required for delivery of effective defibrillation therapy. Of course, if N=1 (i.e., only one far-field EGM channel is utilized), then the steps 26 and 28 are omitted.

Thus, it can be appreciated that with the method of the presently preferred embodiment of the present invention described above, if three or more EGM channels are used (i.e., one near-field EGM channel and two or more far-field EGM channels), the excitable gaps in the different regions of the patient's heart are brought into phase with one another by first entraining the region associated with the near-field EGM channel with the region associated with the closest far-field EGM channel, and then successively entraining the thusly "captured" regions with the regions associated with the remaining EGM channels corresponding to the successively more distant regions of the patient's heart, until all regions and their associated EGM channels are in-phase. In this connection, it is believed that entrainment of the higher regions facilitates entrainment of the lower VG regions by propagation of the electrical stimuli through the previously entrained higher VG regions.

When the regions associated with all EGM channels are in-phase, the excitable gaps in each of the plurality of VG regions of the heart will also be in-phase, thereby rendering all of these different VG regions of the patient's heart responsive to electrical stimuli at the same time. Thus, after the regions associated with all EGM channels are brought into phase with one another, the ventricular fibrillation is either intrinsically converted into ventricular tachycardia, which can be terminated by delivery of any known cardioversion therapy, or is terminated by delivery of any known defibrillation therapy.

The present invention also encompasses a cardiac therapy device (e.g., an ICD) programmed to implement the method of the present invention for delivering cardiac therapy described hereinabove. In general, although presently preferred embodiments of the present invention have been described in detail hereinabove, it should be clearly understood that many variations and/or modifications of the basic inventive concepts herein taught which may appear to those skilled in the pertinent art will still fall within the spirit and scope of the present invention, as defined in the appended claims.

What is claimed is:

1. A method for delivering cardiac therapy, including the steps of:
    generating a first signal indicative of cardiac activity in a first region of a patient's heart;
    generating a second signal indicative of cardiac activity in a second region of the heart; and,
    bringing the first and second signals into phase alignment with one another to thereby bring the first and second regions into phase alignment with one another.

2. The method as set forth in claim 1, wherein the first signal comprises a first electrogram and the second signal comprises a second electrogram.

3. The method as set forth in claim 2, wherein the step of generating a first signal is carried out by using a first sensing electrode located proximate the first region of the heart, and the step of generating a second signal is carried out by using a second sensing electrode located proximate the second region of the heart.

4. The method as set forth in claim 2, wherein the first electrogram comprises a first digitized waveform indicative of successive activations and excitable gaps therebetween which occur in the first region of the heart, and the second electrogram comprises a second digitized waveform indicative of successive activations and excitable gaps therebetween which occur in the second local region of the heart.

5. The method as set forth in claim 4, wherein the step of bringing the first and second signals into phase alignment with one another includes the sub-steps of:
    comparing the relative phases of the first and second digitized waveforms at a prescribed phase comparison time;
    in response to the comparing step, determining whether the first and second digitized waveforms are in-phase, or whether the phase of the first digitized waveform leads or lags the phase of the second digitized waveform;
    if it is determined that the phase of the first digitized waveform leads the phase of the second digitized waveform, then delivering an electrical stimulus to the heart at a first time appropriate to extend the refractory period in the first region of the heart, to thereby reduce the phase difference between the first and second regions; and,
    if it is determined that the phase of the first digitized waveform lags the phase of the second digitized waveform, then delivering an electrical stimulus to the heart at a second time appropriate to advance the timing of the next activation in the first region of the heart, to thereby reduce the phase difference between the first and second regions.

6. The method as set forth in claim 5, wherein:
    the step of determining is carried out by further determining the phase difference, if any, between the first and second digitized waveforms at the prescribed phase comparison time; and,
    the step of delivering an electrical stimulus to the heart is carried out by delivering an electrical stimulus having a voltage proportional to the determined phase difference.

7. The method as set forth in claim 5, wherein the step of bringing the first and second signals into phase alignment with one another further includes the sub-steps of:
   if it is determined that the first and second digitized waveforms are in-phase, then determining the cardiac status of the patient; and,
   delivering the appropriate cardiac therapy for the determined cardiac status.

8. The method as set forth in claim 5, wherein the second time is during a late repolarization phase of an activation which occurs in the first region of the heart.

9. The method as set forth in claim 5, wherein the second time is during an excitable gap which occurs in the first region of the heart.

10. The method as set forth in claim 5, wherein the first time is during a refractory period of an activation which occurs in the first region of the heart.

11. A method for delivering cardiac therapy using a cardiac therapy device implanted in a patient having a plurality N of sensors positioned proximate respective voltage gradient regions of the patient's heart for generating respective electrograms, the method including the steps of:
   determining the relationship of a phase of a first one of the electrograms with a phase of an ith one of the electrograms, wherein i=1 through N;
   if it is determined that the phase of the first one of the electrograms leads the phase of said ith one of the electrograms, then delivering an electrical stimulus to the patient's heart at a first time appropriate to reduce the phase difference between the phases of the first and with one of the electrograms;
   if it is determined that the phase of the first one of the electrograms lags the phase of the ith one of the electrograms, then delivering an electrical stimulus to the patient's heart at a second time appropriate to reduce the phase difference between the phases of said first and ith one of the electrograms;
   if it determined that the phase difference between the phases of the first and ith electrograms is less than a prescribed amount, then incrementing i;
   determining whether i=N, and if i≠N, then repeating the above-recited and present steps, until it is determined that i=N.

12. The method as set forth in claim 11, further including the step of, after it is determined that i=N, determining the cardiac status of the patient and delivering the appropriate cardiac therapy for the determined cardiac status.

13. The method as set forth in claim 11, wherein:
   the first one of the electrograms comprises an electrogram generated by a one of the sensors nearest a pulse delivery electrode; and,
   the ith ones of the electrograms comprise electrograms generated by respective ones of the sensors further from the pulse delivery electrode.

14. The method as set forth in claim 11, wherein:
   the electrograms comprise waveforms indicative of successive activations and excitable gaps therebetween which occur in the respective voltage gradient regions of the patient's heart; and,
   the first time is during a refractory period which occurs in a first voltage gradient region of the patient's heart.

15. The method as set forth in claim 14, wherein the second time is during a late repolarization phase which occurs in the first voltage gradient region of the patient's heart.

16. The method as set forth in claim 14, wherein the second time is during an excitable gap which occurs in the first voltage gradient region of the patient's heart.

17. A cardiac therapy device for delivering cardiac therapy to a patient having a plurality N of sensors positioned proximate respective voltage gradient regions of the patient's heart for generating respective electrograms, comprising:
   signal processing circuitry for receiving the electrograms;
   pulse delivery circuitry for delivering electrical stimuli to the patient's heart in response to control signals generated by the signal processing circuitry; and,
   wherein the signal processing circuitry determines the relationship of a phase of a first one of the electrograms with a phase of an ith one of the electrograms, wherein i=1 through N, and if it is determined that the phase of the first one of the electrograms leads the phase of the ith one of the electrograms, then generating a first control signal for causing the pulse delivery circuitry to deliver an electrical stimulus to the patient's heart at a first time appropriate to reduce the phase difference between the phases of the first and ith one of the electrograms; and if it is determined that the phase of the first one of the electrograms lags the phase of the ith one of the electrograms, then delivering a second control signal for causing the pulse delivery circuitry to deliver an electrical stimulus to the patient's heart at a second time appropriate to reduce the phase difference between the phases of the first and ith one of the electrograms.

18. The cardiac therapy device as set forth in claim 17, wherein:
   the first one of the electrograms comprises an electrogram generated by a one of the sensors nearest a pulse delivery electrode; and,
   the ith ones of the electrograms comprise electrograms generated by respective ones of the sensors further from the pulse delivery electrode.

19. The cardiac therapy device as set forth in claim 16, wherein:
   the electrograms comprise waveforms indicative of successive activations and excitable gaps therebetween which occur in the respective voltage gradient regions of the patient's heart; and,
   the first time is during a refractory period of an activation which occurs in a first voltage gradient region of the patient's heart.

20. The cardiac therapy device as set forth in claim 19, wherein the second time is during a late repolarization phase which occurs in the first voltage gradient region of the patient's heart.

21. The cardiac therapy device as set forth in claim 20, wherein the second time is during an excitable gap which occurs in the first voltage gradient region of the patient's heart.

22. A method for delivering cardiac therapy, including the steps of:
   generating a first signal indicative of cardiac activity in a first region of a patient's heart;
   generating a second signal indicative of cardiac activity in a second region of the heart; and,
   selectively shortening or lengthening an activation interval in at least one of the first and second regions, based on the first and second signals.

23. The method as set forth in claim 22, wherein the first signal comprises a first electrogram and the second signal comprises a second electrogram.

24. The method as set forth in claim 23, wherein the step of generating a first signal is carried out by using a first sensing electrode located proximate the first region of the heart, and the step of generating a second signal is carried out by using a second sensing electrode located proximate the second region of the heart.

25. A method for delivering cardiac therapy, including the steps of:

generating a first signal indicative of cardiac activity in a first region of a patient's heart;

generating a second signal indicative of cardiac activity in a second region of the heart; and, selectively lengthening a refractory period in at least one of the first and second regions, based on the first and second signals.

26. The method as set forth in claim 25, wherein the first signal comprises a first electrogram and the second signal comprises a second electrogram.

27. A cardiac therapy device for delivering cardiac therapy to a patient having a plurality of sensors positioned proximate respective voltage gradient regions of the patient's heart for generating respective electrograms, comprising:

signal processing circuitry for receiving the electrograms and for determining a relationship between the electrograms;

pulse delivery means for delivering electrical stimuli to the patient's heart in response to control signals generated by the signal processing circuitry; and, wherein the signal processing circuitry generates a first control signal for causing the pulse delivery means to deliver an electrical stimulus to the patient's heart at a first time appropriate to shorten an activation interval in at least one of the voltage gradient regions in response to a first relationship between the electrograms, and generates a second control signal for causing the pulse delivery means to deliver an electrical stimulus to the patient's heart at a second time appropriate to extend an activation interval in at least one of the voltage gradient regions in response to a second relationship between the electrograms.

* * * * *